United States Patent
Pope et al.

(10) Patent No.: US 8,182,461 B2
(45) Date of Patent: May 22, 2012

(54) SYRINGE PUMP RAPID OCCLUSION DETECTION SYSTEM

(75) Inventors: Brian Pope, Suwanee, GA (US); Zhan Liu, Atlanta, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 1978 days.

(21) Appl. No.: 10/700,738

(22) Filed: Nov. 4, 2003

(65) Prior Publication Data

US 2005/0096593 A1     May 5, 2005

(51) Int. Cl.
*A61M 31/00* (2006.01)
(52) U.S. Cl. .......................................... 604/503; 604/67
(58) Field of Classification Search .............. 604/65–67, 604/890.1
See application file for complete search history.

(56) References Cited

U.S. PATENT DOCUMENTS

| | | | |
|---|---|---|---|
| 4,882,575 A | 11/1989 | Kawahara | |
| 5,178,603 A | 1/1993 | Prince | |
| 5,501,665 A * | 3/1996 | Jhuboo et al. .................. | 604/65 |
| 5,935,106 A | 8/1999 | Olsen | |
| 6,368,314 B1 | 4/2002 | Kipfer et al. | |
| 6,423,035 B1 | 7/2002 | Das et al. ....................... | 604/155 |
| 6,485,465 B2 * | 11/2002 | Moberg et al. ................. | 604/154 |
| 6,572,604 B1 | 6/2003 | Platt et al. | |
| 6,620,151 B2 | 9/2003 | Blischak et al. | |
| 6,648,861 B2 | 11/2003 | Platt et al. | |
| 6,659,980 B2 | 12/2003 | Moberg et al. | |
| 6,966,895 B2 | 11/2005 | Tribe | |
| 2002/0016569 A1 | 2/2002 | Critchlow et al. | |
| 2003/0205587 A1 * | 11/2003 | Tribe et al. .................... | 222/420 |

FOREIGN PATENT DOCUMENTS

| | | |
|---|---|---|
| EP | 1 188 454 A | 7/2001 |
| EP | 1188454 A2 | 3/2002 |
| JP | 9-512472 | 12/1997 |
| WO | 8705225 A2 | 9/1987 |
| WO | 92/02264 A1 | 2/1992 |
| WO | 9627398 A1 | 9/1996 |
| WO | 9952575 | 10/1999 |
| WO | WO 01/72357 A | 10/2001 |
| WO | 02/38204 A2 | 5/2002 |

OTHER PUBLICATIONS

*Partial European Search Report* for EP 04 25 6588 dated Mar. 15, 2005.
*International Search Report* for PCT/US2004/034960 mailed Mar. 21, 2005.
European Search Report from related European Application No. EP 08 07 5178, dated Apr. 28, 2008 (3 pages).
Written Opinion from related European Application No. EP 08 07 5178, dated Apr. 28, 2008 (3 pages).

* cited by examiner

*Primary Examiner* — Kevin C Sirmons
*Assistant Examiner* — Andrew Gilbert
(74) *Attorney, Agent, or Firm* — Wood, Herron & Evans, LLP

(57) ABSTRACT

An apparatus, method and program product detects an occlusion in a fluid line by determining if a relationship between force measurements departs from an expected relationship.

70 Claims, 6 Drawing Sheets

| SYRINGE SIZE (CC) | INFUSION RATE (ML/HR) | SLOPE RATE |
|---|---|---|
| 1 | .02 | .2 |
| 3 | .04 | .4 |
| 5 | .05 | .7 |
| 10 | .08 | .8 |
| 20 | .2 | .9 |
| 30 | .3 | .4 |
| 60 | .2 | .8 |

SYRINGE PUMP RAPID OCCLUSION DETECTION SYSTEM

FIELD OF THE INVENTION

The present invention relates to drug infusion pumps, and more particularly, to detecting an occlusion in the fluid path of such pumps.

BACKGROUND OF THE INVENTION

The administration of many medications requires specific dosing regimens that occur over a relatively long period of time. To this end, the development of syringe pumps has dramatically benefited patients needing volumetrically proportioned delivery of their medication. Syringe pumps generally comprise a barrel, or syringe, and mount to a housing. The syringe is typically filled with one or more chemical, nutritional or biological substances that are mixed into a uniform solution. A pusher associated with the pump forces a plunger through the syringe. As the plunger travels through the syringe, the medication is forced out into flexible tubing and/or catheters and into the patient.

During the course of delivering the medication to the patient, it is possible for an occlusion to arise in the delivery path. Examples of occlusions may include a closed stopcock, slider valve or pinched line. Such a condition, if undetected, may cause injury to the patient. That is, when an occlusion occurs along the delivery path, medication is not delivered to the patient even though the pump continues to function. Thus, an occlusion prevents the infusion pump from delivering medication to the patient until the occlusion can be detected and cleared from the infusion path. For this reason, the rapid detection of occlusions along the delivery path is key to reliable pump operation.

An occlusion in the infusion line will cause the force, or pressure, in the syringe to increase. In turn, force between the pusher of the syringe pump and the syringe plunger will increase. Conventional pumping systems use a transducer to monitor force between the pusher of the syringe pump and the syringe plunger, or the pressure in the syringe. Other more costly pumping systems position a disposable sensor within the actual delivery line.

In such prior art pumps, an alarm is generated when the force between the pusher and the plunger or the pressure in the syringe increases above a predetermined threshold. As such, the alarm is either "on" or "off" depending on whether the threshold has been met. As a consequence, the user has no way to know whether the pressure in the syringe is building up to an unacceptable level that precedes the threshold. The user only knows when the alarm is reached. Thus, remedial action can only be taken once an infusion protocol has already been potentially compromised.

This circumstance is compounded where the threshold is set to a relatively high value to avoid false occlusion alarms. At low delivery rates, a conventional pump may take hours to reach high enough line pressure to trigger conventional alarm systems. This detection period delay would ideally be around five minutes or less to avoid having a negative impact on patient care.

Still another obstacle to occlusion detection arises in the context of bolus injections, where a relatively large volume of medication is delivered in a relatively short period of time. In such bolus applications, the pressure in the pump will easily exceed the threshold alarm level, irrespective of the presence or absence of an actual occlusion. Similarly, widely varying pressures that occur during the initial, ramping stage of a non-bolus delivery render conventional detection methods unreliable in the face of varying flow rates. Thus, it is extremely difficult to detect whether the deliver line is occluded during stages of both bolus and non-bolus pumping applications.

As a consequence, there exists a need for an improved manner of automatically detecting an occlusion within a fluid line with a medical infusion system.

SUMMARY OF THE INVENTION

The present invention provides an improved apparatus, program product and method for automatically detecting an occlusion in a fluid line of a medical infusion system in a manner that overcomes the problems of conventional pumps. In one sense, the invention detects a trend that is indicative of an occlusion much earlier than is possible with known practices. For example, processes of the present invention typically allow detection of closed stopcocks, slider valves, pinched lines and other occlusions in about five minutes or less (based on a delivery rate of 1 ml/hr with a 60 ml syringe).

Such occlusion detection results are made possible using existing transducers present in most pumps, and thus do not require additional hardware. Moreover, occlusions are detected under a wide variety of circumstances and without a propensity of false occlusions. To this end, the pressure values of a force sensor are monitored over time spaced intervals. The pressure values may be processed to generate a slope, which is compared to value comprising an expected relationship. If the comparison is unfavorable, an occlusion alarm is initiated.

In more particularly determining the presence of an occlusion, first and second pressure values are obtained at times T1 and T2, respectively. A relationship between the pressure values is determined. This relationship typically comprises a slope. An occlusion is indicated if this relationship between the first and second pressure values departs from an expected relationship. For instance, the trial slope determined from the pressure values may be greater than an occlusion slope recalled from memory. The recalled slope is optimized for the purpose of detecting an occlusion as a product of syringe size, type and fluid delivery rate, among other clinically established factors.

In accordance with a further aspect of the invention, a steady state condition of the infusion system is determined to improve system reliability. Steady state processes consistent with the principles of the present invention accommodate the wide pressure variance that occurs during initial ramp up. In so doing, the steady state processes account for a period of system operation ranging from the start of an infusion application to some determinable point where the initial operating stage of the application should normally have completed.

If an occlusion occurs after steady state has been achieved, the slope determined from the pressure values climbs with respect to time. If this ramp-up in pressure continues for a minimum duration to the extent it departs from the expected relationship, the system determines that an occlusion has occurred.

Another or the same embodiment that is consistent with the principles of the present invention allows an occlusion to be detected during a bolus injection, despite the elevated and widely varying pressure levels associated with such applications. In one sense, movement of the plunger is halted during a bolus infusion whenever a detected value deviates from an expected relationship. Where so desired, the movement of the plunger may continue after some delay time and/or at a reduced infusion rate. Allowing the pressure in the system to relax for a period equal to a delay time limit, in combination with the reduced rate, enables a bolus infusion in a manner that does not exceed the occlusion limit and/or initiate a false occlusion alarm. That is, the intermittent infusion (switch-on/switch-off) bolus feature reduces incidences of false occlusion, while enabling bolus applications at maximum infusion rates.

By virtue of the foregoing, there is thus provided an improved mechanism for automatically detecting an occlusion in a fluid line of a syringe pumping system adapted to carry fluid under pressure to a patient. These and other objects and advantages of the present invention will be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION

Figure 1:
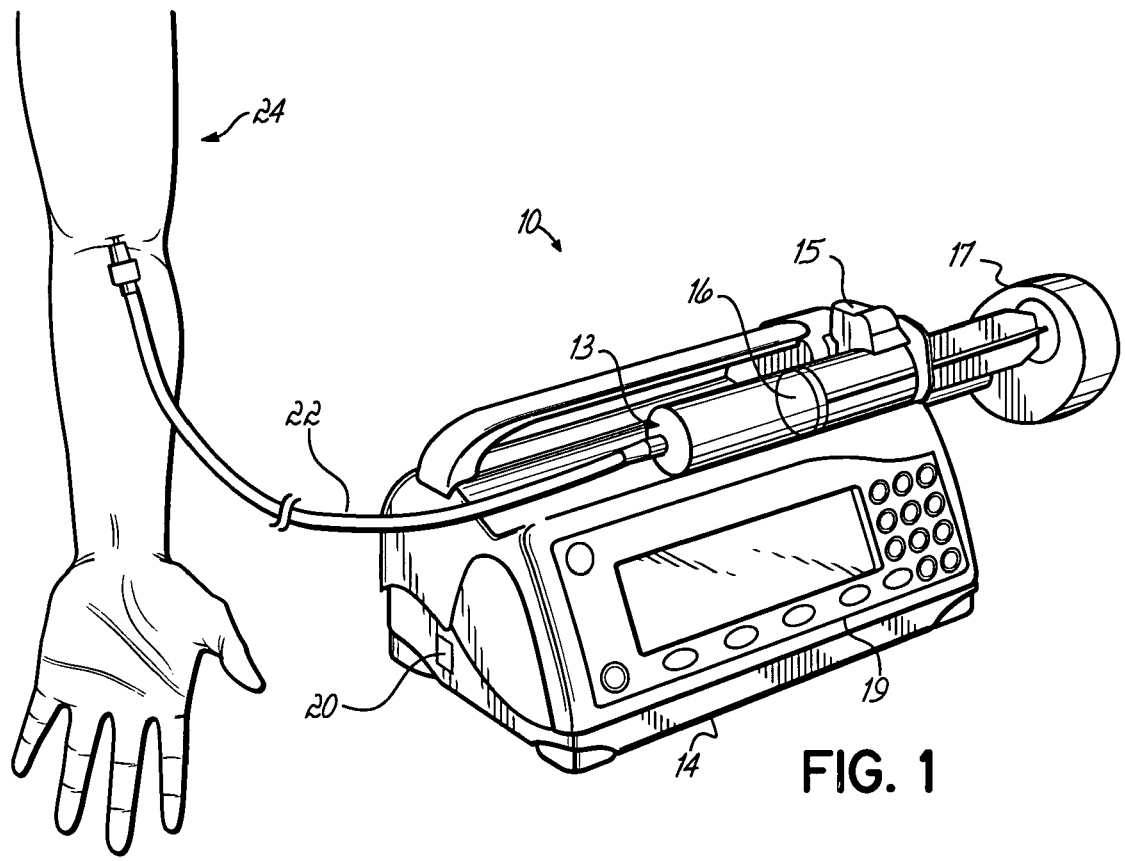
FIG. 1 is a block diagram of a syringe pump system configured to automatically detect an occlusion in a fluid line of the system.

FIG. 1 shows an exemplary syringe pump system 10 configured to automatically detect an occlusion. The system 10 shown in FIG. 1 includes a pharmaceutical cartridge, or syringe 13, which is supported on and secured by housing 14 and clamp 15, respectively. The syringe 13 includes a plunger 16 that regulates the flow of fluid to a patient 24 via infusion line 22. That is, the plunger 16 comprises a piston-type drive mechanism that is internal to the housing 14 and urges the fluid contents out of an outlet of the syringe 13 along the infusion line to the patient 24.

To this end, a motor internal to the housing 14 actuates a pusher, or plunger driver mechanism 17, to move the plunger 16. A sensor, which is typically internal to the plunger driver mechanism 17, monitors fluid force as desired per system specifications. The pump housing 14 may additionally include a display 19 and a communications port 20. A typical display 19 may include operator interface input mechanisms, such as a keyboard, touch screen features, switches, a microphone, dials, and the like. The communications port 20 may include a communications interface for additional equipment, including laptops, handheld programming devices and/or networking equipment. For instance, the communications port 20 of the pump housing 14 may accommodate RS-232 cabling.

While generally not shown in FIG. 1, one that is skilled in the art will recognize that the exemplary system 10 may include additional infusion lines, as well as valve mechanisms, clamps, caps, stopcocks, connectors and additional sensors as per system specifications.

The syringe 13 drives medication into the downstream infusion line 22 at a controlled rate. The head of the plunger 16 is typically retained in such a way as to allow the plunger 16 to be pushed in, but to prevent the plunger 16 from moving in of its own accord as a result of siphoning of fluid from the syringe barrel. For instance, the plunger 16 may be retained by means of wedge-like arms that move across the forward surface of the head of the plunger 16 and force the rear surface of the plunger head against a forward facing surface of the plunger head retainer so as to formally clamp it against the surface.

The display 19 may include options for a user to enter input. Such input may include data pertaining to drug concentration, patient weight, as well as desired doses and dose rates. The digital communication port 20 provides a mechanism for external control, where desired. For instance, the pump housing 14 may be continuously cabled to a separate remote personal computing device. One skilled in the art will appreciate that wireless communications may be alternatively used. In any case, this personal computing device can then run a particular program tailored to provide the desired pattern of drug delivery appropriate to the specific circumstance.

Figure 2:
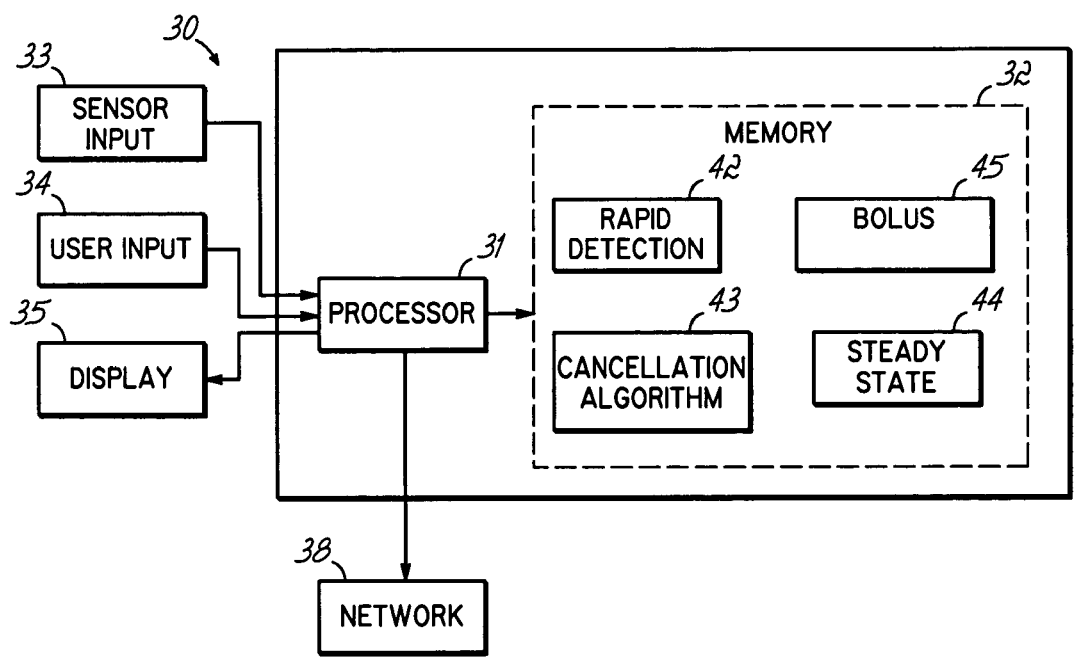
FIG. 2 is a block diagram of an exemplary hardware and software environment for a pump component of the system of FIG. 1.

Regardless of the source of the input, the processor 31 contained within the pump housing 14 may initiate the volume and fluid flow rates to be delivered to the patient. FIG. 2 illustrates a hardware and software environment for a system 30 having such a processor 31 configured to detect an occlusion. As discussed herein, the processor 31 may monitor for an occlusion using input from a sensor 33. A sensor, for purposes of this disclosure, may include any device configured to detect a value indicative of force. A suitable processor may include any device configured to process an electronic signal.

The processor 31 of the system 30 typically couples to a memory 32. As discussed herein, processor 31 may represent one or more processors (e.g., microprocessors), and memory 32 may represent the random access memory (RAM) devices comprising the main storage of the system 30, as well as any supplemental levels of memory, e.g., cache memory, non-volatile or backup memories (e.g., programmable or flash memories), read-only memories, etc. In addition, memory 32 may be considered to include memory storage physically located elsewhere in the system 30, e.g., any cache memory in a processor 31, as well as any storage capacity used as a virtual memory, e.g., as stored within mass storage or on a computer coupled to the system 30 via a network 38. As discussed below in greater detail, stored data may include syringe type, size, infusion rate and slope information, as well as force values. The processor 31 may execute various computer software applications, components, programs, objects, modules, etc. (e.g., rapid detection program 42, cancellation program 43, steady state program 44, and bolus program 45, among others).

In general, the routines executed to implement the embodiments of the invention, whether implemented as part of an operating system or a specific application, component, program, object, module or sequence of instructions will be referred to herein as "program s." The programs typically comprise one or more instructions that are resident at various times in the system 30. When a program is read and executed by a processor 31, the program causes the system 30 to execute steps or elements embodying the various aspects of the invention.

Moreover, while the invention has and hereinafter will be described in the context of a fully functioning system 30, those skilled in the art will appreciate that the various embodiments of the invention are capable of being distributed as a program product in a variety of forms, and that the invention applies equally regardless of the particular type of signal bearing media used to actually carry out the distribution. Examples of signal bearing media include, but are not limited to recordable type media such as volatile and non-volatile memory devices, floppy and other removable disks, hard disk drives, optical disks (e.g., CD-ROM's, DVD's, etc.), among others, and transmission type media such as digital and analog communication links.

In addition, various programs described hereinafter may be identified based on the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Those skilled in the art will recognize that the exemplary environments illustrated in FIGS. 1 and 2 are not intended to limit the present invention. Indeed those skilled in the art will recognize that other alternative hardware and/or software environments may be used without departing from the scope of the invention.

Figure 3:
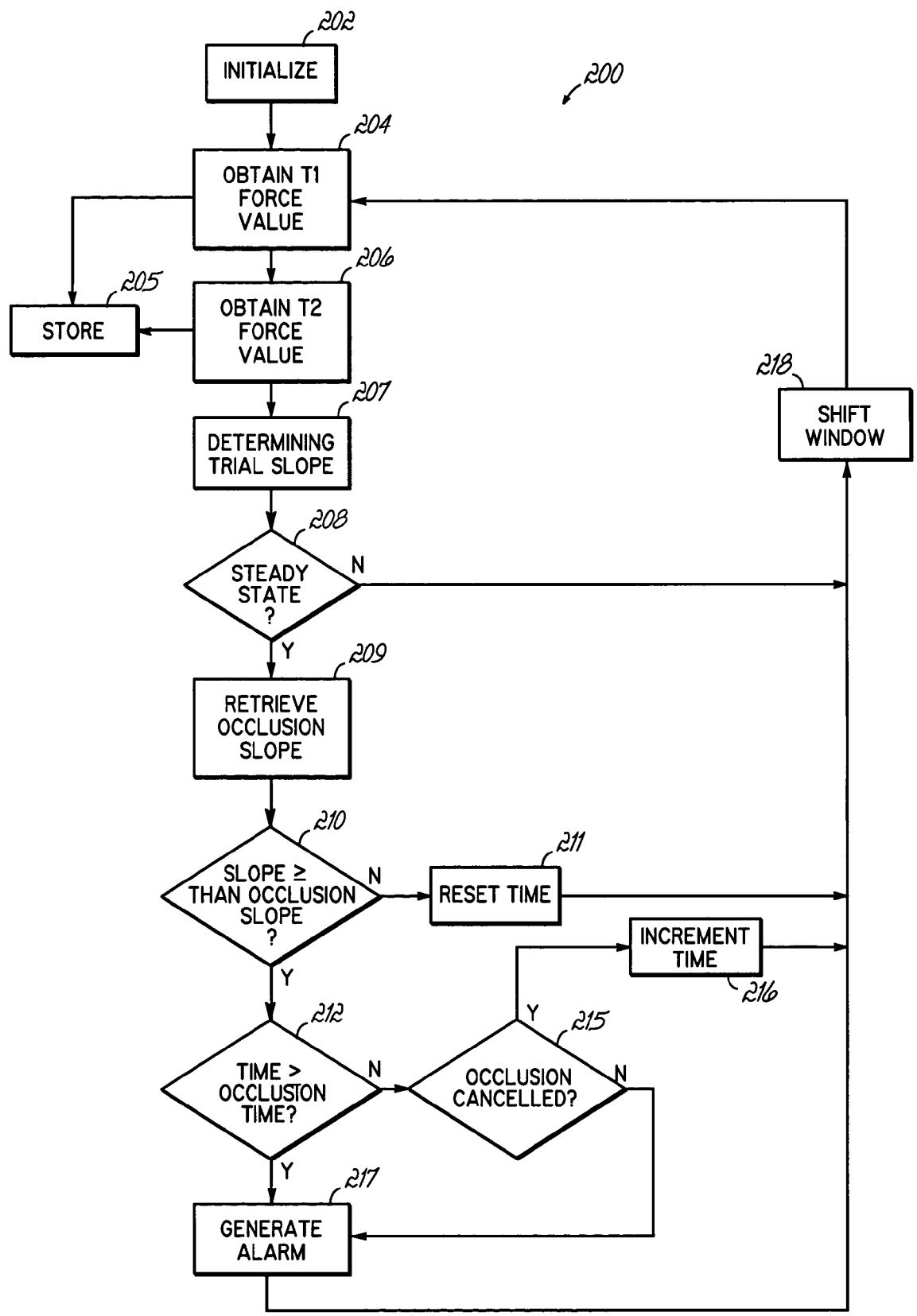
FIG. 3 is a flowchart having method steps suitable for rapidly detecting an occlusion within the system of FIG. 1.

FIG. 3 shows exemplary method steps suited for execution within the hardware environments of FIGS. 1 and 2. More particularly, the flowchart 200 of FIG. 3 includes steps for automatically detecting an occlusion within a fluid line of a medical infusion system during a pumping sequence. The system 10 initializes at block 202 of FIG. 3. The initialization step of block 202 may include or be preceded by connecting a personal computer to the communications port 20 of the housing 14. Thus, the system 10 may include external processing devices configured to connect to the port 20 as discussed herein.

The initialization of block 202 may include user specified infusion protocols, operating parameters and other data. For instance, the user may select one or more fluid flow rates or sequences may be selected based on a desired pattern of drug delivery that is appropriate to the protocol of the patient. Alternatively or additionally, certain parameters may be factory set and/or automatically retrieved from memory or prior use. For example, an earlier infusion protocol may be retrieved where an infusion sequence is to be repeated for a patient.

Initialization may include recalling or defining an expected relationship. This expected relationship may include an occlusion slope. Such a slope may be predetermined using clinical data. For instance, force measurements may be taken under known laboratory conditions at the beginning and end of a window interval. These force measurements are divided by the window to determine the occlusion slope. Some such slopes may be stored in an associative relationship with one or more of the known conditions as applicable to a given pumping system scenario. For instance, a slope may be stored in associative relationship with a particular type or size of syringe, and/or a given infusion rate. As discussed in greater detail in the text describing FIG. 6, the occlusion slope may be determined as a function of a steady state slope detected in a given patient application.

Where desired, system parameters can be set at block 202 to tolerate "stic ky" syringes and handle glitches in force caused by various conditions, including a change in force due to repositioning of the height of a pump, or the change in delivery rate of another pump that is feeding the same delivery path.

Another setting accomplished at or prior to block 202 of FIG. 3 may include specifying or recalling an appropriate window size. The window size may define the interval(s) at which force readings, or values, are to be accomplished. Put another way, a window includes first and second force values communicated from the force sensor 33 to the processor 31. As discussed herein, a relationship between these force values is compared to an expected relationship to determine the presence of an occlusion. That is, the relationship is later compared to the expected relationship to determine whether an occlusion should be declared.

Still another exemplary parameter that is set at or prior to block 202 of FIG. 3 may include an occlusion detection time. The occlusion detection time may define a minimum period of time required to determine whether an occlusion has occurred. For instance and as discussed in greater detail below, an occlusion slope or other unexpected relationship may have to be sustained for at least a period equal to the defined occlusion detection time before an occlusion will be declared.

Block 202 of FIG. 3 may be additionally include initiating an infusion at a specified infusion rate. For instance, a medicated fluid may begin to flow at block 202 at an infusion rate of 5 ml/hr.

At block 204 of FIG. 3, the system 10 obtains or otherwise determines a first force value. This first force value may be obtained at a time, T1, for instance. As discussed herein, time T1 may be stipulated by parameters input at or prior to block 202. While a suitable force value may comprise any measurement indicative of force present within the system 10, a typical force value includes a binary output from a transducer in communication with the force sensor. Such a transducer may comprise an analog-to-digital converter, for instance. As such, an electronic signal from the force sensor is processed by the transducer to generate an output.

The output from the A/D converter thus varies according to the force detected by the force sensor. For example, a force reading of two PSI may cause the A/D converter to output a binary value of 76 mV. This voltage output may later be converted to a "count" unit for processing considerations. Either or both the output and count comprise force values for purposes of this specification and may be stored at block 205 for later use.

A subsequent, second force value may be obtained at block 206. This second force value may be accomplished in a fashion similar to that of block 204 at time, T2. As before, time T2 may be predetermined as part of an infusion application setup. Where desired, this second force value is stored also at block 205. While steps for determining only two force values are shown at blocks 204 and 206, one of skill in the art will appreciate that additional force value measurements may be taken in accordance with the principles of the present invention. That is, more than two force values may be used to determine a relationship that is compared to the expected relationship.

The system 10 at block 207 of FIG. 3 uses the force values obtained at blocks 204 and 206 to determine a relationship between them. For instance, the system 10 may determine a slope at block 207. More particularly, the difference between the obtained force values may be divided by the difference in the times that the respective force values were obtained. One or more force values may be stored at block 205 for later use.

Prior to proceeding to another step associated with detecting an occlusion, the system 10 at block 208 may determine if steady state has been achieved. While discussed more particularly in connection with FIG. 6, steady state includes a status of the system 10 at which initial conditions of an infusion application will generally have less impact on occlusion determination processes. One such exemplary initial condition may include an amplified force reading attributable to the normal and relatively sudden influx of fluid into a tube 22 at the onset of an infusion application. A determination of steady state may thus include, for instance, verification that a pump has been primed and/or that a time or fluid volume limit has been exceeded. This step of block 208 reduces the possibility of initial conditions triggering a false occlusion.

The occlusion slope specified at block 202 of FIG. 3 is retrieved at block 209 by the system 10. Such an occlusion slope may comprise the expected relationship as discussed herein. At block 210 of FIG. 3, the retrieved occlusion slope is compared to the trial slope determined at block 207. More particularly, if the determined slope is less than the occlusion slope retrieved at block 209, then the system 10 may not declare an occlusion and may merely continue to monitor for an occlusion. For instance, the system 10 may shift the detection window and obtain additional force values at blocks 218, 204, and/or 206 to determine a new trial slope at block 207. One embodiment that is consistent with the principles of the present invention may additionally reset clock or other counter tracking time at block 211.

Should the detected or other trial slope alternatively be greater than or equal to the retrieved occlusion slope/expected relationship at block 210, the system 10 may determine at block 211 if an occlusion has been canceled. While discussed in greater detail below as the subject of FIG. 7, such a cancellation may occur where, for instance, an occlusion cancellation slope is determined subsequent to the slope determination of block 207. Cancellation of an occlusion may result in the reset at block 213 of a clock or other counter tracking the passage of time associated with an occlusion detection application. Such a count may be useful for determining when an occlusion detection time has been reached.

More particularly, where no cancellation has occurred at block 211, it may be determined at block 212 whether a period corresponding to the occlusion detection time has expired. As discussed herein, the occlusion detection time may be defined as a minimum duration in which an occlusion slope must be sustained in order to declare an occlusion. Step 212 is accomplished, in part, to mitigate occurrences of false occlusions. Namely, an alarm is not generated at block 217 until the occlusion time has expired at block 212. The application counter continues to increment at block 216 until the occlusion time is reached or some other condition intervenes.

Where the detected slope is greater than or equal to the occlusion slope, and the occlusion detection time has lapsed at block 212, the system 10 will generate an occlusion alarm at block 217. While a typical alarm may include an audible signal and/or a flashing display 19, a suitable alarm may comprise any indicator configured to communicate an occlusion status to a user.

As with all of the flowcharts disclosed in this specification, one of skill in the art will appreciate that any of the exemplary steps 202-218 of the flowchart 200 of FIG. 3 may be omitted, rearranged, and/or augmented with additional steps in accordance with the principles of the present invention. Moreover, one of skill in the art will appreciate that the functions of these steps 202-218 of the flowchart 200 may be realized in software and/or hardware environments different than those described in connection with FIGS. 1 and 2.

Figures 4, 5:
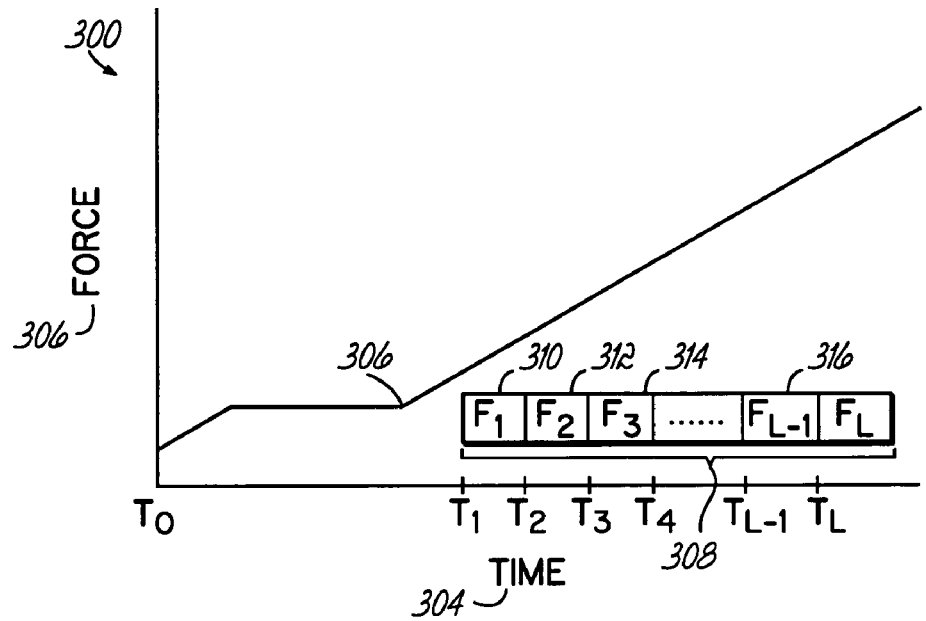
FIG. 4 is a graph plotting pressure values provided by a force sensor of FIG. 1.
FIG. 5 is a table showing exemplary contents of a database having application within a memory component of FIG. 2.

FIG. 4 shows a graph 300 that plots force along its y-axis 302 against time along its x-axis 304. The resultant, plotted line 306 reveals a slope that is indicative of the pressure, or force, within the system 10 as a function of time. For purposes of this specification, "force" and "pressure" may be used interchangeably. In the above-discussed embodiment, the slope of the line 306 may be compared to an expected slope to determine if an occlusion alarm should be initiated. In one sense, an embodiment of the present invention capitalizes on the fact that the slope experienced by a system 10 in occlusion may exhibit steady and predictable characteristics.

As shown in FIG. 4, force measurements are accomplished at windows 310-316. A window for purposes of this specification may comprise two or more time measurements, to include multiple smaller window increments and measurements. More particularly, window 310 may begin at time T1 and ends at time T2. Window 312 correspondingly picks up at time T2 and ends at time T3. While advantageous in certain applications, one of skill in the art should appreciate that such windows need not be consecutive and may be accomplished at any preset and/or random interval. For example, a suitable window may additionally comprise a period between T2 and $T_{L-1}$. In any case, the system 10 may buffer or otherwise store multiple force values 308 in a window buffer.

The size of each window 310-316 may be adjusted to meet any number of system requirements. For instance, the size, or time spanning a window 310 may be adjusted to eliminate or otherwise account for fractions of counts. For example, the size of a first window 310 may be adjusted such that its size will generally detect all of the count data occurring between T1 and T2. Such precaution may avoid instances where the transducer outputs, for example, a sixth count at the border of window 312, where most of the force associated with the sixth count was actually generated in the time span of window 310. As such, the window size may be expanded or contracted to avoid fractional readouts. Continuing with the above example, the size of the windows 308 may be expanded such that the sixth count registers in window 310. In any case, other processing and conversionary applications as appreciated by one skilled in the art may be employed to achieve desired readouts, irrespective of window size.

As discussed herein, each force value may comprise a count from the transducer/analog-to-digital converter over a time span defined by the window size, T1-T2. For instance, a window having a time span of one minute may generate 76 counts. Thus, the counts are indicative of force within the system 10, and may be used along the y-axis 302 of FIG. 4 for use in plotting against time 304. The resultant slope may comprise a relationship that is later compared to an expected relationship to determine the presence or absence of an occlusion.

FIG. 5 shows an exemplary database structure 380 that has application with embodiments of the present invention. For instance, the structure 380 may comprise a lookup table accessible to programs 42-45 that are consistent with the present invention. Such a lookup table may include fields for syringe size 382, infusion rate 384 and slope rate 386 data, among other criteria. For instance, other suitable criteria may include the nature of the substance being infused, the concentration or dissolution of the substance in the fluid, fluid viscosity; the recipient, including sex, age and physical attributes, the occurrence of change in measurable diagnostics related to the actions or effects of the substance being infused, drug concentration predictability, as well as local practices, policies, protocols and regulations or other considerations, including operator judgment. Indeed, one of skill in the art should recognize that any criteria relating to an infusion process may be additionally or alternatively included within or affect the contents of a memory structure that is consistent with the underlying principles of the present invention.

An embodiment of the present invention processes the data contained within the database fields 382 and 384 as input by the user to determine an expected relationship, or slope rate 386. This slope rate 386, which may comprise and/or be converted to counts per minute, may be recalled from memory 32 at block 209 of FIG. 3, for example.

Figure 6:
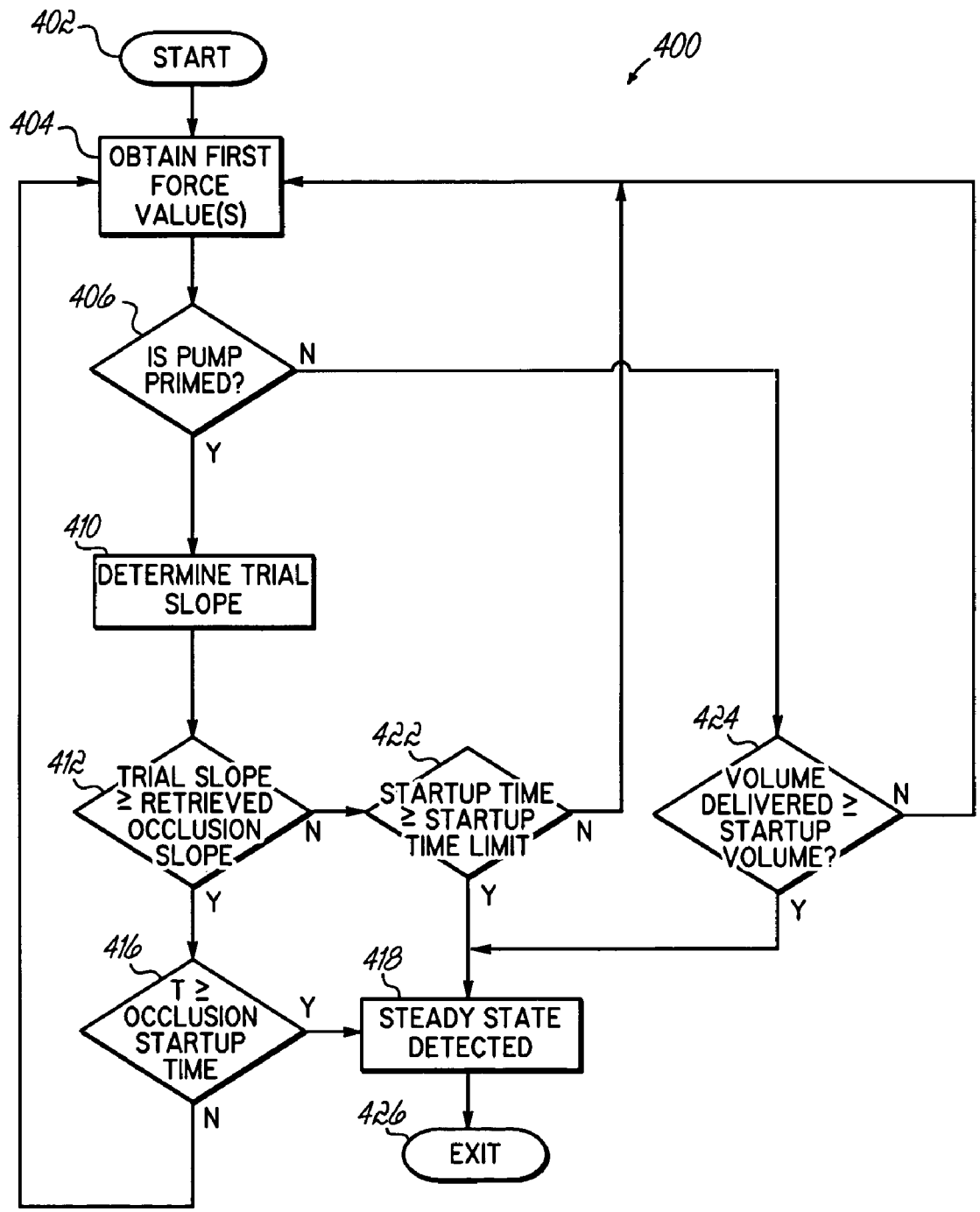
FIG. 6 is a flowchart having method steps suited to detect steady state of the system of FIG. 1.

FIG. 6 shows exemplary method steps suited for determining if steady state has been achieved. At the onset of an infusion process, an initial slope is generated that approaches or exceeds an occlusion slope. This elevated force level may be caused by the tubing 22 and other components of the system 10 reacting to a sudden influx, or ramping up, of pumped fluid. That is, some time is required by the system 10 in order to adjust and achieve a relaxed flow of fluid toward the patient 24. Given time, pressure/force within the system 10 eventually and relatively relaxes in the absence of an occlusion. That is, the force levels off to a more moderate slope. This period of leveling generally coincides with the system 10 achieving steady state.

The processes of the flowchart 400 of FIG. 6 accommodate the initial influx of fluid into the system 10, while mitigating false occurrences of occlusion alarms. The system 10 generally uses the steady state detection processes shown in FIG. 6 to determine when steady state has been achieved. For instance, when a slope generated as a product of the actual force over time is below or equal to an expected occlusion or steady state detection slope. Some embodiments may require the detected slope to last over some minimum occlusion time before declaring steady state or an occlusion. The same or another embodiment of a system 10 that is consistent with the present invention may declare steady state upon the expiration of some designated startup time or in response to an infused volume level.

Steady state detection is enabled at block 402. Initialization processes at block 402 may include user and/or factory specified parameters, such as a minimum time for occlusion, a startup time, steady state slope and a startup volume.

The system 10 determines or otherwise obtains force values at block 404. As discussed herein, an exemplary force value may comprise a count output from an analog-to-digital converter in communication with a force sensor. The force value may be detected by a force or pressure sensor in communication with the downstream infusion tube 22, for instance.

The system 10 may determine whether the pump system 10 is primed at block 406. Priming the pump may include the user pushing a button on a display 19 that initializes the steady state detection processes, along with elevating pressure within the system 10 to an acceptable level. Should the pump not be primed as such at block 406, the steady state detection algorithm 44 may declare steady state where the volume of fluid that has been delivered is greater than a startup volume. The volume delivered and/or the startup volume may be determined as a function of time and the infusion rate. Where such a condition at block 424 is determined to exist, then steady state may be declared at block 418. Otherwise, additional force values may be obtained at block 404. As discussed herein, such force values may be numerous as per system specifications and conditions.

The system 10 may determine a trial slope at block 410 using the force values obtained at block 404. This determined, actual, or trial slope may be compared to a slope retrieved from memory 32. While the retrieved slope may comprise the occlusion slope in one embodiment, another may retrieve a steady state slope having some other appropriate value.

Should the slope determined at block 410 be greater than or equal to the retrieved slope as determined at block 412, then the system 10 may determine at block 416 if a steady state startup time has been exceeded. The steady state startup time may comprise a time period after which steady state will be declared at block 416. This specified startup time limit includes a time at which elevated startup slopes associated with a pre-steady state timeframe normally level off. That is, the startup time may comprise some preset period in which normal (non-occlusion), pre-steady state conditions should have resolved themselves. Where such a startup time limit has been met or exceeded at block 416, the system may declare steady state at block 418. Otherwise at block 416, the system 10 may continue to determine force values at block 404 until the startup time limit or another condition has been met.

Should the slope determined at block 410 fail to meet or exceed the occlusion slope at block 412, the system may rely on time-based analysis at block 422 to determine if some specified startup time limit has expired. Where such a startup time limit has been met or exceeded at block 416, the system may declare steady state at block 418.

Once steady state has been detected, the system 10 may progress into another aspect of occlusion detection as discussed herein. Upon exiting steady state at block 426, for example, the determined slope will then be compared to the same or another (non-steady state) occlusion slope to determine if an occlusion is present within the system 10.

Figure 7:
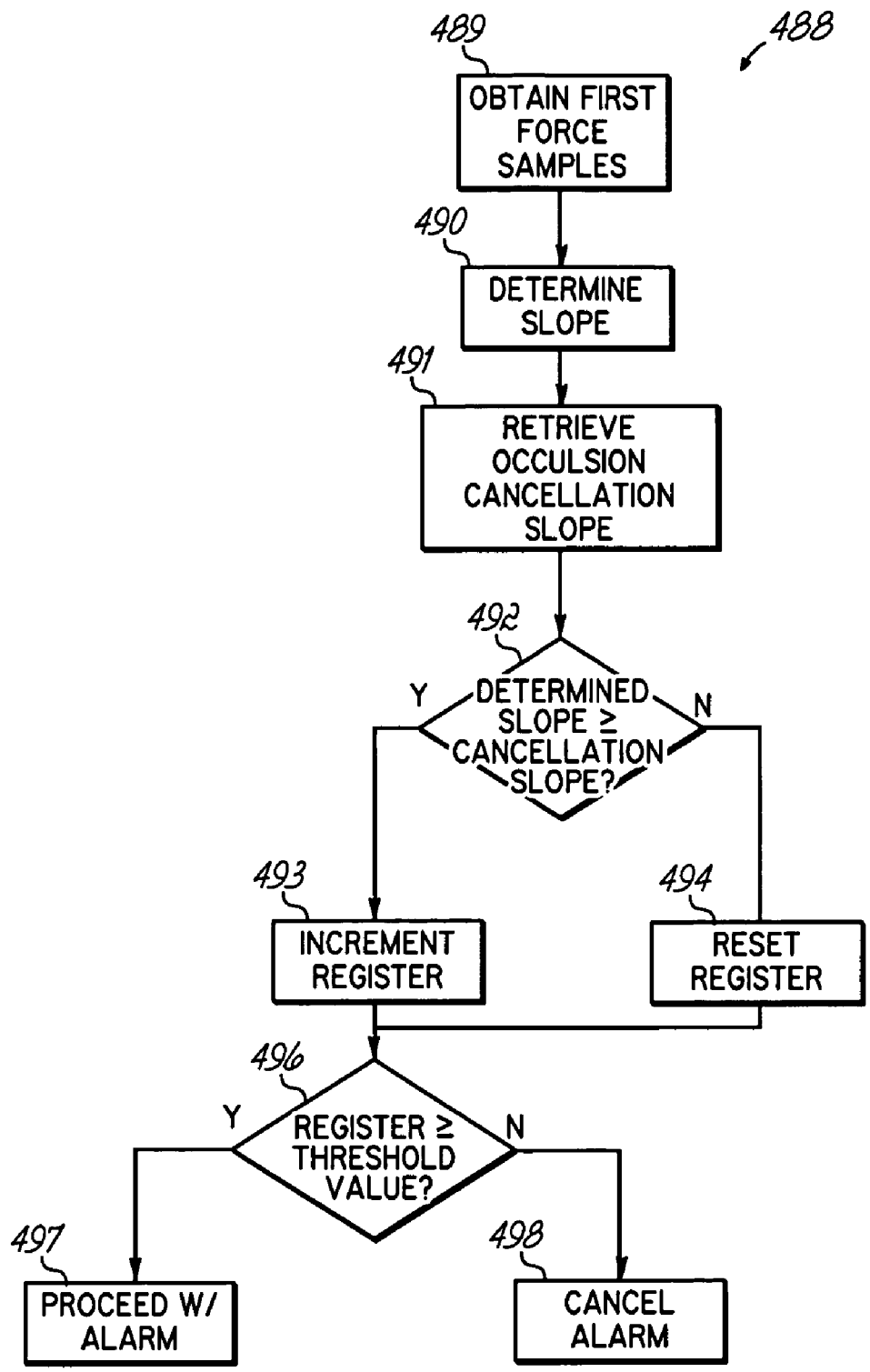
FIG. 7 is a flowchart having method steps for determining if an occlusion alarm step of FIG. 3 should be cancelled.

Flowchart 488 of FIG. 7 outlines exemplary process steps 489-498 that further expound upon the occlusion cancellation step 215 of FIG. 3. That is, the method steps shown in FIG. 7 function to cancel an occlusion alarm and help mitigate incidences of false occlusions. At block 489 of FIG. 7 the system 10 obtains force samples. These force samples include force values as discussed above and may be retrieved from memory or a force sensor. As throughout this specification, multiple force samples may be used to determine the presence or absence of an occlusion.

A trial slope or other relationship is determined at block 490 of FIG. 7. The slope may reflect force values over time as shown and discussed above in connection with FIG. 4.

At block 491, an occlusion cancellation slope value may be retrieved. The occlusion cancellation slope may be predetermined and specified by a user in a manner similar to the occlusion slope discussed in connection with FIG. 3. That is, the occlusion cancellation slope may account for such factors as syringe size, type and the rate of infusion, among other factors. The occlusion cancellation slope is typically smaller than or equal to the occlusion slope. That is, detection of the occlusion cancellation slope represents a departure from the relatively steeper slope associated with an occlusion, e.g., a lessening of force within the system 10.

The system 10 may compare at block 492 the slope determined at block 490 of FIG. 7 with the occlusion cancellation slope retrieved at block 491. More particularly, the system 10 may determine if the trial slope is greater than or equal to the cancellation occlusion slope. If this condition is satisfied at block 492, then the system may increment a register a block 493. A register for purposes of this specification may include any count and be realized in either a software and/or a hardware environment.

Alternatively, should the determined slope be less than the occlusion cancellation slope as determined at block 492 of FIG. 7, the register is not incremented at block 494. In another or the same embodiment, the register may be reset at block 494 in response to the occlusion cancellation slope being greater than the determined slope.

The register may be compared to a threshold value at block 496 at the expiration of an occlusion cancellation time. The threshold value and occlusion cancellation times may be preset by a user. As with all settings discussed herein, these settings may be modified in the field by users to reflect preferences. In the exemplary step of block 496 of FIG. 7, where the register is greater than or equal to the threshold value, the system 10 may proceed with an occlusion alarm at block 497. Alternatively at block 498, the occlusion alarm may be canceled in response to the threshold value equaling or being greater than the current value contained within the register. Such condition may arise, for instance, where a temporary increase in force has resulted from a corresponding change in the elevation of a patient, not an occlusion.

Figure 8:
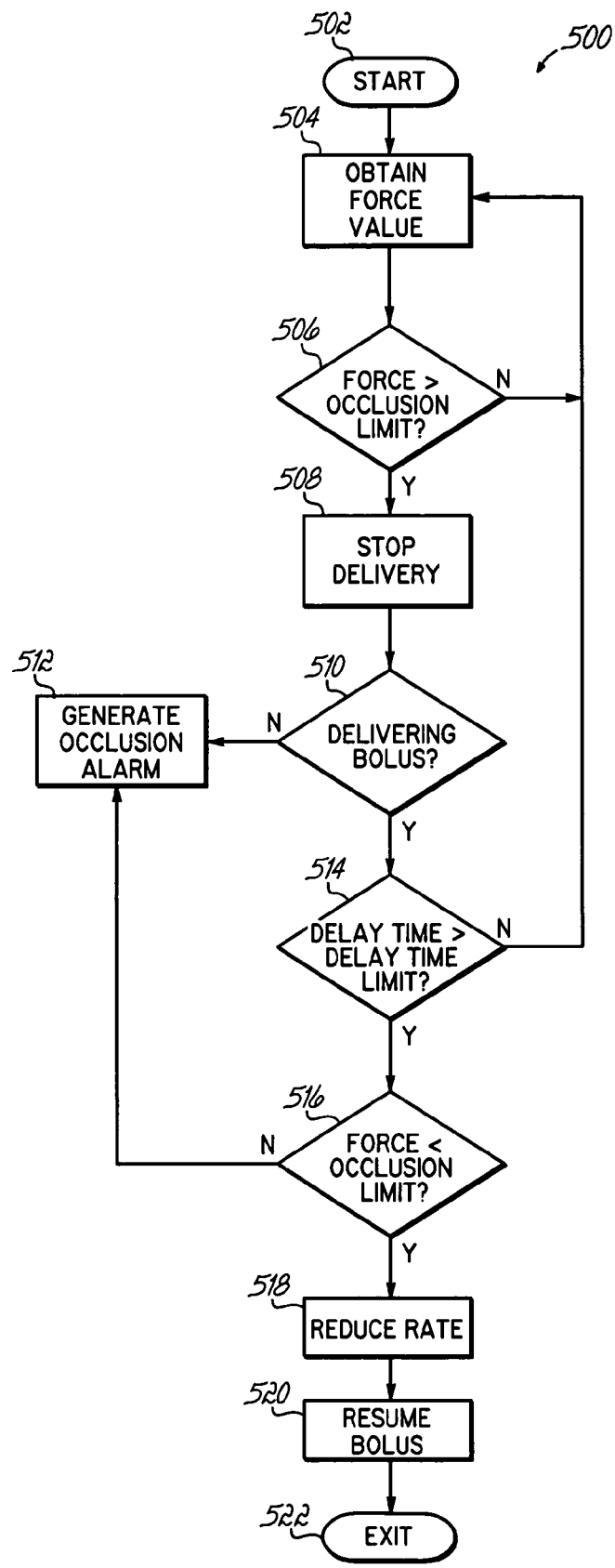
FIG. 8 is a flowchart having method steps suitable for delivering a bolus by the syringe pump system of FIG. 1.

The flowchart 500 of FIG. 8 shows additional processes configured to detect an occlusion within an infusion system 10. The exemplary process steps are particularly suited for application within the context of a bolus injection. Bolus injections present unique challenges with regard to occlusion detection, since the high volumes and infusion rates associated with bolus injections are conventionally difficult to discern from occluded conditions.

The user may initialize the system 10 at block 502 of FIG. 8. Initialization processes may include setting a bolus occlusion limit. As discussed below, a bolus occlusion limit may be a value that functions as a gauge for activating features of the occlusion detection processes of the present invention. Other settings accomplished at block 502 may include setting a delay time as discussed below. The initialization processes of block 502 may presume that a user has connected a personal computer or other processing device to a pump. Such a scenario may be appropriate where desired interface hardware is not included within the pump housing, for instance. Initialization at block 502 may also include commencing infusion of medication. For example, a user may instruct the system 10 to pump fluid at a rate of 600 ml/hr for a given bolus injection.

The system 10 obtains a force value at block 504. The force value may comprise a count output from an analog-to-digital converter. For instance, the system 10 may register 112 counts within the time span of one minute. However, one skilled in the art will appreciate that any value indicative of force within the system 10 may be alternatively used.

The system 10 determines if the obtained force value is greater than the occlusion limit at block 506. The occlusion limit may be set at any value. Where the obtained force value is less than the occlusion limit, then the system may continue to monitor force readings at block 504.

In the flowchart 500 of FIG. 8, the processor 31 of the system 10 may pause, interrupt, decrease, stop or otherwise alter travel of the plunger 16 (and delivery of the fluid) at block 508 in response to determining that the force value obtained at block 504 is greater than the occlusion limit, or expected value, as defined at block 502. One of skill in the art will appreciate that while complete halting of the plunger 16 at block 508 is desired in most cases, another embodiment consistent with the invention may merely slow, reduce or otherwise alter delivery at block 508.

The system 10 may verify that it is operating in bolus delivery mode at block 510. This step at block 510 allows the bolus infusion processes to work within the context of normal, non-bolus infusions. More particularly, if the system determines at block 510 that a bolus is not being delivered, then an occlusion alarm may be generated at block 512. As with other embodiments of the present invention, detection of an occlusion at block 512 may initiate remedial action. Such action may include verifying the function of the system 10, as well as adjusting flow rate and other infusion parameters to compensate for a potential occlusion.

If, however, the user has indicated at block 502 that a bolus is being delivered, then a clock or other counter is monitored at block 514. More particularly, the processor 31 may determine at block 514 whether a span of time from when delivery was stopped at block 508 now exceeds or equals a period specified at block 502 as the set delay time limit. This delay time limit may be set to a duration that will allow the force within most systems to decrease below the occlusion limit in the absence of an occlusion. In the embodiment of FIG. 8, additional force values are obtained at block 504 prior to the clock delay time limit being reached at block 514.

Continuing with FIG. 8, the system 10 determines at block 516 if the current force value is less than the occlusion limit. As above, the occlusion limit value may be retrieved from memory 32 prior to or at step 516. If the current force in the system remains greater than the occlusion limit at block 516, then an occlusion alarm may be generated at block 512. Otherwise, the bolus infusion is resumed at block 520. That is, travel of the plunger 16 resumes and fluid delivery resumes at its former or a different rate.

As suggested by block 518 of FIG. 8, embodiments of the present invention may resume the bolus at a reduced rate. As such, it should be appreciated by one with skill in the art that other embodiments may resume a bolus infusion at block 520 at the prior or any other infusion rate.

Allowing the force in the system 10 to relax for a period equal to the delay time limit, in combination with the reduced rate feature of block 518, enables a bolus infusion in a manner that does not exceed the occlusion limit and/or initiate a false occlusion alarm. That is, the switch-on and switch-off bolus features of blocks 508-520 of FIG. 8 reduce incidences of false occlusion, while enabling bolus applications at maximum infusion rates. In any case, the occlusion detection processes end at block 522.

One of skill in the art will appreciate that the sequence of the steps in all of the included flowcharts may be altered, to include omitted processes without conflicting with the principles of the present invention. Similarly, related or known processes can be incorporated to complement those discussed herein. It should be further understood that any of the embodiments and associated programs discussed above are compatible with most known infusion processes and may be fully optimized to realize even greater efficiencies.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while this specification focused generally on a syringe pump, one skilled in the art will recognize that the underlying principles of the present invention apply equally to other medical pumping systems, to include cassette based and peristaltic pumps. Additionally, while force transducers are discussed above in connection with several embodiments, pressure transducers may have equal or greater applicability in other others that are consistent with the principles of the present invention. For instance, a sensor comprising a pressure transducer may be used at the outlet of a syringe or in the tubing.

Moreover, while embodiments discussed herein generally relate to downstream occlusion, they may apply equally to upstream occlusion detection. As such, a fluid source may comprise a syringe, as well as a bag located upstream. Furthermore, one of skill in the art will appreciate that all slope, time and other value comparisons used to determine the presence of an inclusion may be configured such that either a higher or lower value will trigger a given process. For instance, an alarm of one embodiment may be initiated in response to a determined slope being lower or higher than an expected slope, depending on how the system 10 is configured.

Additionally, while slope determinations serve well for relational comparisons, a suitable expected relationship may alternatively comprise any value indicative of force within the system. In one embodiment, a suitable expected relationship may be a product of both slope and window size. As such, the system 10 may maintain a number of force sensor readings in a buffer or other memory 32. A difference in force sensor readings may be compared to the product of the slope and window size to determine if an inequality or other relationship exists. For example, if the difference in force values is greater than or equal to the product of the slope and window size, then a detection count may be incremented by one. Otherwise, the detection count register may remain unchanged or be reset to zero. When the increment detection count register contents are greater than or equal to those of another occlusion detection counter, an occlusion is declared.

Moreover, one of skill in the art will appreciate that while the processes of the present invention may achieve occlusion detection with only a single force sensor, embodiments that are consistent with the principles of the present invention may include multiple force sensors and sensor positions. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A method of automatically detecting an occlusion in a fluid line of a syringe pump, the syringe pump including a housing adapted to support a syringe containing a plunger moveable inside the syringe by pushing an end of a plunger with a pusher to expel fluid from an outlet of the syringe into a fluid line connected to the outlet and configured to carry the fluid under pressure to a patient, the method comprising:
   mounting the syringe onto the housing with the plunger end extended;
   coupling the pusher to the end of the plunger;
   initiating a pumping sequence to cause the fluid to flow into the fluid line;
   during the pumping sequence, using a sensor to determine a first instantaneous force value F1 indicative of force in the fluid line at instantaneous time T1;
   during the pumping sequence, determining a second instantaneous force value F2 indicative of force in the fluid line at instantaneous time T2; and
   providing an indication of the occlusion if a slope calculated by dividing a difference between the second instantaneous force value F2 and the first instantaneous force value F1 by a difference between instantaneous time T1 and instantaneous time T2 departs from an expected slope relationship.

2. The method of automatically detecting an occlusion of claim 1, further comprising providing no occlusion indication where the calculated slope does not depart from the expected slope relationship.

3. The method of automatically detecting an occlusion of claim 1, further comprising determining a steady state condition.

4. The method of automatically detecting an occlusion of claim 1, further comprising determining a time window defining at least one of time T1 and time T2.

5. The method of automatically detecting an occlusion of claim 1, wherein providing the indication of the occlusion further includes determining the expected slope relationship.

6. The method of automatically detecting an occlusion of claim 1, wherein providing the indication of the occlusion further includes determining a trial slope using at least one of the first and second instantaneous force values.

7. The method of automatically detecting an occlusion of claim 1, wherein providing the indication of the occlusion further includes determining an occlusion slope.

8. The method of automatically detecting an occlusion of claim 1, wherein providing the indication of the occlusion further includes comparing the expected slope relationship to the calculated slope.

9. The method of automatically detecting an occlusion of claim 1, wherein providing the indication of the occlusion further includes comparing an occlusion slope to a trial slope.

10. The method of automatically detecting an occlusion of claim 1, further comprising shifting a time window to obtain an additional instantaneous force value.

11. The method of automatically detecting an occlusion of claim 1, further comprising canceling the indication of the occlusion in response to a comparison between a trial slope and a cancellation slope.

12. A method of automatically detecting an occlusion in a fluid line of a medical pumping system, the fluid line being configured to carry fluid under pressure between a fluid source and a patient, the method comprising:
   during a pumping sequence, determining a first instantaneous force value F1 indicative of force in the fluid line at instantaneous time T1;
   during the pumping sequence, determining a second instantaneous force value F2 indicative of force in the fluid line at instantaneous time T2; and
   providing an indication of the occlusion if a slope calculated by dividing a difference between the second instantaneous force value F2 and the first instantaneous force value F1 by a difference between instantaneous time T1 and instantaneous time T2 departs from an expected slope relationship.

13. The method of automatically detecting an occlusion of claim 12, further comprising providing no occlusion indication where the calculated slope does not depart from the expected slope relationship.

14. The method of automatically detecting an occlusion of claim 12, further comprising determining a steady state condition.

15. The method of automatically detecting an occlusion of claim 14, wherein determining the steady state condition further includes determining a steady state startup time period.

16. The method of automatically detecting an occlusion of claim 15, wherein determining the steady state condition further includes determining a startup time limit.

17. The method of automatically detecting an occlusion of claim 15, wherein determining the steady state condition further includes determining a startup fluid volume.

18. The method of automatically detecting an occlusion of claim 12, wherein determining at least one of the first and second instantaneous force values further includes using a sensor.

19. The method of automatically detecting an occlusion of claim 12, wherein determining at least one of the first and second instantaneous force values further includes determining a count indicative of the at least one of the first and second instantaneous force values.

20. The method of automatically detecting an occlusion of claim 19, further comprising adjusting at least one of time T1 and time T2 to avoid fractioning the count.

21. The method of automatically detecting an occlusion of claim 19, further comprising using a transducer to generate the count.

22. The method of automatically detecting an occlusion of claim 12, further comprising determining a time window defining at least one of time T1 and time T2.

23. The method of automatically detecting an occlusion of claim 12, wherein providing the indication of the occlusion further includes generating an alarm.

24. The method of automatically detecting an occlusion of claim 12, wherein providing the indication of the occlusion further includes determining the expected slope relationship.

25. The method of automatically detecting an occlusion of claim 12, wherein providing the indication of the occlusion further includes determining a trial slope using at least one of the first and second instantaneous force values.

26. The method of automatically detecting an occlusion of claim 12, wherein providing the indication of the occlusion further includes determining an occlusion slope.

27. The method of automatically detecting an occlusion of claim 12, wherein providing the indication of the occlusion further includes comparing the expected slope relationship to the calculated slope.

28. The method of automatically detecting an occlusion of claim 12, wherein providing the indication of the occlusion further includes comparing an occlusion slope to a trial slope.

29. The method of automatically detecting an occlusion of claim 12, further comprising shifting a time window to obtain an additional instantaneous force value.

30. The method of automatically detecting an occlusion of claim 12, further comprising canceling the indication of the occlusion in response to a comparison between a trial slope and a cancellation slope.

31. The method of automatically detecting an occlusion of claim 12, wherein determining the first instantaneous force value further includes altering delivery of the fluid.

32. The method of automatically detecting an occlusion of claim 12, wherein determining the first instantaneous force value further includes altering delivery of the fluid in response to comparing the first instantaneous force value to a bolus occlusion limit.

33. The method of automatically detecting an occlusion of claim 32, wherein determining the first instantaneous force value further includes resuming delivery of the fluid after a delay time.

34. The method of automatically detecting an occlusion of claim 32, wherein determining the first instantaneous force value further includes resuming delivery of the fluid in response to comparing the first instantaneous force value to a bolus occlusion limit.

35. The method of automatically detecting an occlusion of claim 12, wherein providing the indication of the occlusion further includes initiating a remedial action.

36. A syringe pumping system, comprising:
a syringe configured to contain fluid and including an outlet;
a housing adapted to support the syringe;
a plunger having an end and configured to move within the syringe;
a pusher adapted to attach to and push the end of the plunger so as to cause the fluid to exit out of the outlet of syringe;
a fluid line connected to the outlet of the syringe and configured to carry the fluid under force to a patient;
a sensor for determining at least first and second instantaneous force values F1 and F2 indicative of the force between the syringe and the patient taken at instantaneous times T1 and T2, respectively; and
a processor in communication with the pusher, the processor being configured to execute program code that determines if a slope calculated by dividing a difference between the second instantaneous force value F2 and the first instantaneous force value F1 by a difference between instantaneous time T1 and instantaneous time T2 departs from an expected slope relationship.

37. The syringe pumping system of claim 36, wherein the program code initiates providing an indication of an occlusion if the calculated slope departs from the expected slope relationship.

38. The syringe pumping system of claim 36, wherein the program code initiates determining a time window defining at least one of time T1 and time T2.

39. The syringe pumping system of claim 36, wherein the program code initiates determining the expected slope relationship.

40. The syringe pumping system of claim 36, wherein the expected slope relationship includes an occlusion slope.

41. The syringe pumping system of claim 36, wherein the program code initiates comparing the expected slope relationship to the calculated slope.

42. The syringe pumping system of claim 36, wherein the program code initiates comparing an occlusion slope to a trial slope.

43. The syringe pumping system of claim 36, wherein the program code initiates determining a third instantaneous force value indicative of a force between the fluid source and the patient taken at times T2 and T3, respectively.

44. The syringe pumping system of claim 36, wherein the program code initiates determining a third instantaneous force value indicative of a force between the fluid source and the patient taken at times T1 and T3, wherein T3 is subsequent to T2.

45. A pumping system, comprising:
a fluid source;
a fluid line configured to carry fluid under pressure between the fluid source and a patient;
a sensor for determining at least first and second instantaneous force values F1 and F2 indicative of the force between the fluid source and the patient taken at instantaneous times T1 and T2, respectively;
a pump configured to generate a force between the fluid source and the patient; and
a processor in communication with the pump, the processor being configured to execute program code that determines if a slope calculated by dividing a difference between the second instantaneous force value F2 and the first instantaneous force value F1 by a difference between instantaneous time T1 and instantaneous time T2 departs from an expected slope relationship.

46. The pumping system of claim 45, wherein the program code initiates providing an indication of an occlusion if the calculated slope departs from the expected slope relationship.

47. The pumping system of claim 45, wherein the program code initiates determining a steady state condition.

48. The pumping system of claim 45, wherein the program code initiates determining a count indicative of the at least one of the first and second instantaneous force values.

49. The pumping system of claim 45, further comprising a transducer configured to generate a count from at least one of the first and second instantaneous force values.

50. The pumping system of claim 45, wherein the program code initiates determining a time window defining at least one of time T1 and time T2.

51. The pumping system of claim 45, wherein the program code initiates determining the expected slope relationship.

52. The pumping system of claim 45, wherein a relationship between the first and second instantaneous force values includes a trial slope.

53. The pumping system of claim 45, wherein the expected slope relationship includes an occlusion slope.

54. The pumping system of claim 45, wherein the program code initiates comparing the expected slope relationship to the calculated slope.

55. The pumping system of claim 45, wherein the program code initiates comparing an occlusion slope to a trial slope.

56. The pumping system of claim 45, wherein the program code initiates shifting a time window to obtain an additional instantaneous force value.

57. The pumping system of claim 45, wherein the program code initiates canceling the indication of the occlusion in response to a comparison between a trial slope and a cancellation slope.

58. The pumping system of claim 45, wherein the program code initiates altering delivery of the fluid.

59. The pumping system of claim 45, wherein the program code initiates altering delivery of the fluid in response to comparing the first instantaneous force value to a bolus occlusion limit.

60. The pumping system of claim 59, wherein the program code initiates resuming delivery of the fluid after a delay time.

61. The pumping system of claim 59, wherein the program code initiates resuming delivery of the fluid in response to comparing the first instantaneous force value to a bolus occlusion limit.

62. The pumping system of claim 45, wherein the program code initiates determining a third instantaneous force value indicative of a force between the fluid source and the patient taken at times T2 and T3, respectively.

63. The pumping system of claim 45, wherein the program code initiates determining a third instantaneous force value indicative of a force between the fluid source and the patient taken at times T1 and T3, wherein T3 is subsequent to T2.

64. A pumping system, comprising:
a fluid source;
a fluid line configured to carry fluid under force between the fluid source and a patient;
a sensor for determining at least first and second instantaneous force values F1 and F2 indicative of the force between the fluid source and the patient taken at instantaneous times T1 and T2, respectively;
a pump configured to generate the force between the fluid source and the patient; and
a processor in communication with the pump, the processor being configured to execute program code that initiates altering delivery of the fluid in response to determining that a slope calculated by dividing a difference between the second instantaneous force value F2 and the first instantaneous force value F1 by a difference between instantaneous time T1 and instantaneous time T2 deviates from an expected value.

65. The pumping system of claim 64, wherein the program code initiates determining if a bolus infusion is being delivered.

66. The pumping system of claim 64, wherein the program code initiates resuming the delivery of the fluid after a delay period.

67. The pumping system of claim 64, wherein the program code initiates resuming the delivery of the fluid at a reduced infusion rate.

68. A syringe pumping system, comprising:
a syringe configured to contain fluid and including an outlet;
a housing adapted to support the syringe;
a plunger having an end and configured to move within the syringe;
a pusher adapted to attach to and push the end of the plunger so as to cause the fluid to exit out of the outlet of syringe;
a fluid line connected to the outlet of the syringe and configured to carry the fluid under force to a patient;
a sensor for determining at least first and second instantaneous force values F1 and F2 indicative of the force between the fluid source and the patient taken at instantaneous times T1 and T2, respectively; and
a processor in communication with the pusher, the processor being configured to execute program code that initiates altering delivery of the fluid in response to determining that a slope calculated by dividing a difference between the second instantaneous force value F2 and the first instantaneous force value F1 by a difference between instantaneous time T1 and instantaneous time T2 deviates from an expected value.

69. The pumping system of claim 68, wherein the program code initiates determining if a bolus infusion is being delivered.

70. The pumping system of claim 68, wherein the program code initiates resuming the delivery of the fluid after a delay period.

* * * * *